United States Patent [19]

Grob

[11] Plant 4,103

[45] Sept. 13, 1977

[54] KALANCHOE PLANT

[75] Inventor: Adolf Grob, Saint Gall, Switzerland

[73] Assignee: Mikkelsens, Inc., Ashtabula, Ohio

[21] Appl. No.: 709,282

[22] Filed: July 27, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Donald D. Jeffery

[57] ABSTRACT

This invention relates to a novel Kalanchoe having intense orange blossoms of large size which are produced for many weeks.

2 Drawing Figures

The present invention relates to a new and distinctive cultivar of Kalanchoe plant, botanically known as Kalanchoe and known by the cultivar name Sirius, developed by me through controlled breeding by crossing the unpatented cultivar Mars (seed parent) x Rotkappchen (pollen parent), with the latter being disclosed in my U.S. Plant Pat. No. 3,851. Asexual reproduction by stem cuttings of the new cultivar has shown that the unique features of the new Kalanchoe are stabilized and are reproduced true to type in successive propagations.

The following characteristics distinguish Sirius from both its parent varieties and other cultivated Kalanchoes of this type known and used in the floriculture industry:

1. In comparison to Rotkappchen, my new cultivar Sirius is a more vigorous growing cultivar, being a taller and fuller plant by 20% or more when produced under the same growing conditions.

2. When compared to Rotkappchen, the flower color of Sirius is an intense orange and adds a new shade to the Kalanchoes available at the present time. Rotkappchen is orange-red in flower color.

3. Sirius is more free flowering and earlier flowering than Rotkappchen, which heretofore has been the earliest flowering of my present Kalanchoe cultivars.

4. Self branching of Sirius from the base of the plant helps fill out the plant. Most of the lower shoots fully develop flowers.

5. Many individual flowers of Sirius have five petals. Flower size is exceptionally large, being totally as much as 20–22 mm. in diameter.

6. Summer flowering is generally 10 weeks from start of flower induction to 12–13 weeks flowering under poor winter growing conditions.

7. When grown with other Kalanchoes that deteriorate with stem rot in the winter months, Sirius is quite outstanding in that it apparently has great resistance to botrytis stem rot.

8. Cutting production is 20–30 per cent greater than for my cultivars Mars and Rotkappchen.

9. Lower foliage tends to be overly large and massive in summer months thereby necessitating use of growth regulators to facilitate ease of shipping. Leaves cup up along mid-vein. Care must be exercised in watering during winter months to prevent the occurrence of odema on the leaf surface.

10. Flowering plants can be marketed when only a few flowers are in bloom because of the brilliant expression of flower color and well formed umbels that continue to develop over several weeks growth.

The accompanying colored photograph illustrates the overall appearance of this variety taken as a top perspective view of the plant and showing the colors as true as it is reasonably possible to obtain in a colored reproduction of this type.

The following is a detailed description of my new kalanchoe variety based on plants produced under commercial practices at the nursery of Wyss Samen und Pflanzen AG, Zuchwil, Switzerland. Color references are made to the Royal Horticultural Society Colour Chart except where general terms of ordinary dictionary significance are used.

Parentage: Seedling of Mars x Rotkappchen (U.S. Plant Pat. No. 3,851), selected from seed crop of 1972.

Propagation:

*Type cutting.*—Terminal cuttings 10–20 mm. long

*Time to root.*—14–18 days at 22–25° C summer; and 20–24 days at 20° winter.

*Rooting habit.*—Quick abundant rooting with fibrous dendritic roots.

Plant description:

*Form.*—Strong, upright, compact, semi-self branching plant.

*Habit of growth.*—Rapid, vigorous, sometimes having large foliage at the base of the plant being disproportional to the height of the plant.

*Foliage description.*—Tendency to a lighter green than most of my varieties, but of good overall quality and average quantity for commercial Kalanchoes. Size: Up to 12 cm. long by 10 cm. wide, leaf petiole 25–30 mm. long, pronounced cupping, readily fractured when grown January through May. Shape: Elliptical to ovate, apex obtuse, base obtuse. Texture: Glabrous, coriaceous. Margin: Crenate to some double crenate. Color: Mature foliage, top side near 146A, Underside, near 146C.

Flowering description:

*Flowering habits.*—Terminal inflorescence often up to 9 cm. to 10 cm. in diameter, central flowers opening first with flowering continuing for several weeks until total cymes are in flower, with clean floral display for 6 weeks or more; flowers displayed as a compound paniculate cyme.

*Natural flowering season.*—Mid January at 18° C. Flowering time under controlled daylength at 18° to 20° in summer is 10 weeks; in winter is 11–12 weeks. Sirius is considered fast flowering compared to Feuerball and Feuerzauber, disclosed in my U.S. Plant Pat. Nos. 3,861 and 3,853, respectively.

*Flower bud description.*—Long slender, 16–18 mm., reverse underside light orange.

*Flowers borne.*—On strong pedicels branching from thick upright peduncles 10 to 12 cm. high and 5–6 mm. in diameter. Spreading at approximately 30° angle from main stem gives excellent floral placement.

*Quantity of flowers.*—Main terminal compound cymes contain 75 to 90 flowers.

*Petals.*—Shape: Nearly round to oval, pointed 8 to 10 mm. in diameter. Color: Top side when opening, orange-red from 32A to 30A, fading to orange-red 33C, underside red 41-C. Number of petals: Normally four but frequently five, total flower size 20 to 22 mm. in diameter.

*Reproductive organs.*—Stamens: Eight in number. Anther shape: Flat, color light brown; Filament color: Yellow green; Pollen color: Sulphur yellow. Pistils: Total length 13 mm. Stigma shape: Flat, crystalline color, light yellow, cream; Style color: Translucent green; Ovaries: four in number, size 9 mm., color light green.

Disease resistance: No evidence of susceptibility to mildew or winter crown or stem rot.

In summary, this new cultivar appears to be the most vigorous, heaviest stemmed Kalanchoe hybrid I have introduced to date.

It should be noted that environmental conditions such as temperature, light, and especially soil moisture and nutrients greatly affect the size and color of foliage and flowers of Kalanchoes because of their succulent type of growth.

I claim:

1. A new and distinct cultivar of Kalanchoe plant known by the cultivar name Sirius and particularly characterized as to novelty by its vigorous growth; intense orange flower color; early flowering; excellent self branching; exceptionally large total flower size; excellent cutting production; well formed umbels that continue to develop over several weeks growth, and by its apparently great resistance to botrytis stem rot.

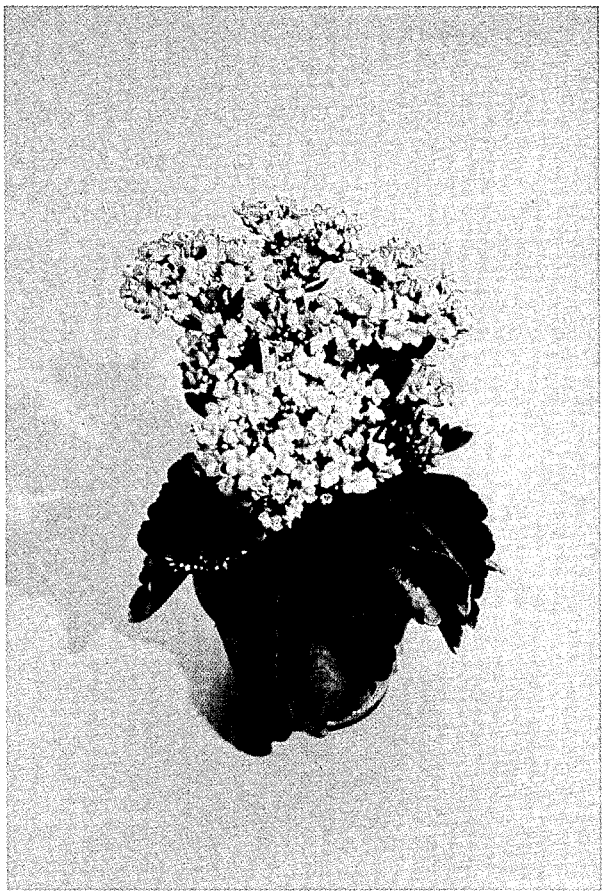

* * * * *